United States Patent [19]

Imperante et al.

[11] Patent Number: 5,300,666
[45] Date of Patent: Apr. 5, 1994

[54] SILICONE ISETHIONATE POLYMERS

[75] Inventors: John Imperante, Lebanon, N.J.; Anthony J. O'Lenick, Jr., Lilburn, Ga.

[73] Assignees: Siltech Inc., Norcross, Ga.; Phoenix Chemical, Somerville, N.J.

[21] Appl. No.: 134,616

[22] Filed: Oct. 12, 1993

[51] Int. Cl.$^5$ .............................. C07F 7/08; C07F 7/18
[52] U.S. Cl. ......................................... 556/428; 554/77
[58] Field of Search .......................... 556/428; 554/77

[56] References Cited

U.S. PATENT DOCUMENTS

| | | | |
|---|---|---|---|
| 3,507,897 | 4/1970 | Kanner et al. | 556/428 |
| 3,513,183 | 5/1970 | Morehouse | 554/77 X |
| 3,531,417 | 9/1970 | Morehouse | 556/428 X |
| 3,531,507 | 9/1970 | Morehouse | 556/428 |
| 3,997,580 | 12/1976 | Morehouse | 556/428 X |
| 4,039,562 | 8/1977 | Bloch et al. | 554/77 |
| 5,068,380 | 11/1991 | Meguriya et al. | 556/428 |

*Primary Examiner*—Paul F. Shaver

[57] ABSTRACT

The present invention relates to a series of novel silicone isethionate polymers, useful as detergents and softeners for hair, and fiber and conditioners skin. The compounds of the present invention are prepared by the reaction of a carboxy silicone with an isethionate to produce novel surface active materials useful in personal care applications like soap bars.

18 Claims, No Drawings

SILICONE ISETHIONATE POLYMERS

BACKGROUND OF THE INVENTION:

(1) Field of Invention

The present invention relates to a series of novel silicone isethionate polymers. These materials are surface active silicone compounds which are useful in a personal care and related applications, Specifically in the formulation of synthetic detergent bars, the so called syndet bars.

Since the compounds of the present invention are high molecular weight silicone polymers, they have a high degree of oxidative stability, even at elevated temperatures. In addition, these compounds are non volatile and non irritating to eyes and skin.

The compounds of the present invention are prepared by the reaction of the hydroxyl group on sodium isethionate with a carboxy silicone.

(2) Object of the Invention

It is the object of the present invention to provide a series of novel silicone isethionate polymers, which are exceptionally mild detergents and which are substantive to skin and hair. This substantivity results in superior softening, conditioning and antistatic properties.

It is another objective of the current invention to provide silicone isethionate derivatives which are non-irritating surface active agents. The compounds of the present invention have very low irritation values when applied to skin and eyes. Irritation is a major problem with traditional surfactants.

Application of the compounds of the invention can be from solvent, aqueous dispersion or solution, or applied neat in these process. It is anticipated that the effective conditioning concentration of the compound of this invention ranges from 0.1% to 25% by weight.

(3) Description of the Arts and Practices

Silicone oils, (polydimethylsiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not bonded the effect is very transient. The product is removed with one washing. Fatty sodium Isethionate derivatives known to those skilled in the art. Sodium isethionate conforms to the following structure:

HO—(CH$_2$)$_2$—SO$_3$M wherein M is a metal ion preferably an alkali metal such as sodium, potassium, ammonium or lithium.

U.S. Pat. No. 4,515,721 issued to Login in May of 1985 teaches one method of producing fatty isethionates. While this patent discloses a new process for preparation of fatty products, there was no attempt to incorporate silicone into compound. Consequently, the unique softening and substantivity properties achieved using the compounds of the present invention are not realized with the above technologies.

THE INVENTION

1) Summary of the Invention

The present invention relates to a series of novel silicone based isethionate surfactants. These silicone polymers have a pendant isethionate functional group present. The polymers by virtue of the pendent group are very mild detergents which also deposit on hair, skin and fiber surfaces forming effective nonvolatile nonirritating, surface modifying finishes. The compounds of the present invention are excellent conditioners, antistats and non-yellowing, softeners.

The compounds of this invention are represented by the following formula;

R—(CH$_2$)$_2$—SO$_3$M wherein
R is

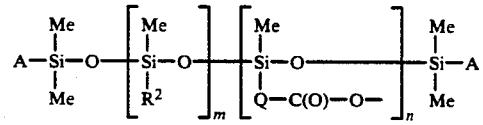

wherein
Me is methyl;
R$^2$ is selected from the group consisting of methyl and phenyl;
Q is (CH$_2$)$_c$;
c is an integer from 3 to 17;
A is selected from the group consisting of methyl and

Q—C(O)—O— m is an integer from 0 to 200;
n is an integer from 1 to 10 when A is methyl;
n is an integer from 0 to 10 when A is —Q—C(O)—O—;
M is selected from the group consisting of Na, K, Li, and NH$_4$.

The products of the present invention are prepared by reaction of a carboxy containing silicone intermediate conforming to the following structure:

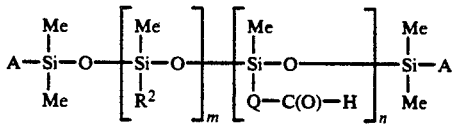

wherein
Me is methyl;
Q is (CH$_2$)$_c$;
c is an integer from 3 to 17;
A is selected from the group consisting of methyl and

m is an integer from 0 to 200;
n is an integer from 1 to 10;
with a an isethionate derivative conforming to the following structure:

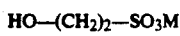

wherein M is selected from the group consisting of Na, K, Li, and NH$_4$.

PREFERRED EMBODIMENTS

In a preferred embodiment n is 1.
In another preferred embodiment n is 2.
In another preferred embodiment n is 3.
In another preferred embodiment n is 4.
In the most preferred embodiment n is 10.
In a preferred embodiment R is alkyl having 12-18 carbon atoms.
In a preferred embodiment M is Na.
In another preferred embodiment M is K.

EXAMPLES

Carboxy Silicone Reactants

Many manufacturers offer a series of carboxy functional silicone compounds suitable for use as raw materials in the preparation of the esters of the present invention. These materials are marketed under the many trade names. Two companies making them are Siltech Inc, and Dow Corning.

The preferred method of placing this type of reactive carboxy group into the silicone polymer is by the reaction of silanic hydrogen containing polymer with a terminal unsaturated carboxylate. This technology is well known to those skilled in the art.

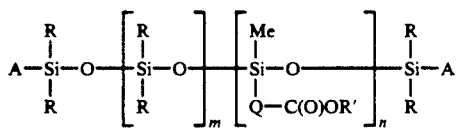

wherein R is methyl;
R' is hydrogen;
Q is (CH$_2$)$_c$;
c is an integer from 3 to 17;
m is an integer from 0 to 200;
n is an integer from 1 to 10;
A is methyl;

| Example | Name        | c  | n  | m   |
|---------|-------------|----|----|-----|
| 1       | Siltech C 1000 | 10 | 3  | 15  |
| 2       | Siltech C 1000 | 10 | 1  | 20  |
| 3       | Siltech C 1200 | 3  | 4  | 50  |
| 4       | Siltech C 1300 | 3  | 2  | 200 |
| 5       | Siltech C 1400 | 4  | 1  | 29  |
| 6       | Siltech C 1500 | 17 | 3  | 1   |
| 7       | Siltech C 1600 | 17 | 4  | 150 |
| 8       | Siltech C 1700 | 4  | 10 | 55  |

Terminal Substituted Carboxy Silicone

Terminal substituted carboxy silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

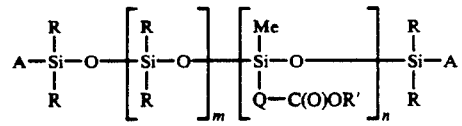

wherein:
R is methyl;
R' is hydrogen;
Q is (CH$_2$)$_c$;
c is an integer from 3 to 17;
n is 0
A is —Q—C(O)OR'
m is an integer from 0 to 200;

| Example | Name          | c  | m   |
|---------|---------------|----|-----|
| 9       | Siltech CT 701 | 10 | 1   |
| 10      | Siltech CT 706 | 3  | 200 |
| 11      | Siltech CT 710 | 17 | 50  |
| 12      | Siltech CT 750 | 10 | 100 |
| 13      | Siltech CT 790 | 3  | 150 |

Isethionate Reactants

Isethionate derivatives are commercially available from many sources. Rhone Poulenc Cranbury, N.J. is one source.

These materials are prepared by the condensation of sodium sulfite and ethylene oxide. The reaction is conducted in water and in a subsequent step the water is evaporated off to produce an essentially anhydrous powder.

The reaction sequence is as follows:

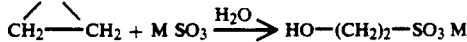

| Example | M Group   | Structure              |
|---------|-----------|------------------------|
| 14      | Sodium    | HO—(CH$_2$)$_2$—SO$_3$ Na |
| 15      | Potassium | HO—(CH$_2$)$_2$—SO$_3$ K  |
| 16      | Lithium   | HO—(CH$_2$)$_2$—SO$_3$ Li |
| 17      | Ammonium  | HO—(CH$_2$)$_2$—SO$_3$ NH$_4$ |

COMPOUNDS OF THE PRESENT INVENTION

General Reaction Procedure

The products of the present invention are generally prepared as follows:

To a suitable flask, equipped with a thermometer and agitator is added the specified amount and type of carboxy silicone. Next add the specified amount of the type of isethionate reactant. Next add 5.0 grams of zinc oxide. The reaction mass blanketed with nitrogen and heated to 220-240 C. and held from between 5 and 15 hours. Water is distilled off which approaches 98% of theoretical before reaction is terminated.

The product can be used as prepared or washed with isopropanol and dried in vacuo.

EXAMPLE 18

To a suitable flask, equipped with a thermometer and agitator is added 609.0 grams type of carboxy silicone example 1. Next add 148.0 grams of sodium isethionate reactant example 14. Next add 5.0 grams of zinc oxide. The reaction mass blanketed with nitrogen and heated to 220-240 C. and held from between 5 and 15 hours. Water is distilled off which approaches 98% of theoretical before reaction is terminated.

EXAMPLES 19-35

Example 18 is repeated only this time the specified amounts and types of silicone reactant and isethionate derivative is added replacing the taurine and silicone reactant used in example 18.

| Example | Isethionate Reactant Example | Grams | Silicone Reactants Example | Grams |
|---|---|---|---|---|
| 19 | 14 | 148.0 | 1 | 609.0 |
| 20 | 15 | 164.0 | 2 | 1827.0 |
| 21 | 16 | 132.0 | 3 | 1051.0 |
| 22 | 17 | 143.0 | 4 | 7570.0 |
| 23 | 14 | 148.0 | 5 | 2409.0 |
| 28 | 14 | 148.0 | 6 | 361.0 |
| 29 | 14 | 100.0 | 7 | 3100.0 |
| 30 | 14 | 125.0 | 8 | 524.2 |
| 31 | 14 | 148.0 | 9 | 290.0 |
| 32 | 14 | 148.0 | 10 | 7553.0 |
| 33 | 14 | 148.0 | 11 | 2200.0 |
| 34 | 14 | 75.0 | 12 | 4000.0 |
| 35 | 14 | 148.0 | 13 | 5700.0 |

Applications Examples

Several of the compounds of the present invention were milled into soap bars at 4%. The soap bar was found to have outstanding slip, lubrication and softening properties, without interfering with the bar's degree of solidness. The bars were rated on a scale of 1-5 for lubrications and softness. The results were as follows:

| Material | 1 (worst) → 5 (best) Rating |
|---|---|
| Soap Bar (no additive) | 1 |
| Example 25 | 4 |
| Example 19 | 4 |
| Example 35 | 5 |

As can be readily seen the addition of the compounds of the present invention to soap bars improves the soft hand and lubrication of the soap.

What is claimed is:

1. A silicone polymer which conforms to the following structure:

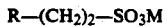

wherein:
R is

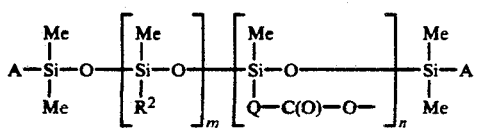

wherein

Me is methyl;
$R^2$ is selected from the group consisting of methyl and phenyl;
Q is $(CH_2)_c$;
c is an integer from 3 to 17;
A is selected from the group consisting of methyl and

—Q—C(O)—O— m is an integer from 0 to 200;
n is an integer from 1 to 10 when A is methyl;
n is an integer from 0 to 10 when A is —Q—C(O)—O—;
M is selected from the group consisting of Na, K, Li, and $NH_4$.

2. A compound of claim 1 wherein M is Na.
3. A compound of claim 1 wherein M is K.
4. A compound of claim 1 wherein M is Li.
5. A compound of claim 1 wherein M is $NH_4$.
6. A compound of claim 1 wherein A is methyl.
7. A compound of claim 1 wherein A is —Q—C(O)—O—.
8. A compound of claim 1 wherein c is 9.
9. A compound of claim 1 wherein c is 3.
10. A compound prepared the esterification reaction of a carboxy containing silicone compound conforming to the following structure:

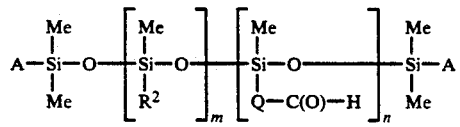

wherein
Me is methyl;
Q is $(CH_2)_c$;
c is an integer from 3 to 17;
A is selected from the group consisting of methyl and

—Q—C(O)—O— n is an integer from 1 to 10 when A is methyl;
n is an integer from 0 to 10 when A is —Q—C(O)—O—
with an isethionate derivative conforming to the following structure:

H—O—$(CH_2)_2$—$SO_3$M wherein
M is selected from the group consisting of Na, K, Li, and $NH_4$.

11. A compound of claim 10 wherein M is Na.
12. A compound of claim 10 wherein M is K.
13. A compound of claim 10 wherein M is Li.
14. A compound of claim 10 wherein M is $NH_4$.
15. A compound of claim 10 wherein A is methyl.
16. A compound of claim 10 wherein A is —Q—C(O)—O—.
17. A compound of claim 10 wherein c is 9.
18. A compound of claim 10 wherein c is 3.

* * * * *